United States Patent
Fugier et al.

(10) Patent No.: US 7,358,372 B2
(45) Date of Patent: Apr. 15, 2008

(54) METHOD FOR THE SYNTHESIS OF PERINDOPRIL AND THE PHARMACEUTICALLY ACCEPTABLE SALTS THEREOF

(75) Inventors: Claude Fugier, Gruchet le Valasse (FR); Thierry Dubuffet, Autretot (FR); Pascal Langlois, Saint Jean de la Neuville (FR)

(73) Assignee: Les Laboratories Servier, Courbevoie Cedex (FR)

( * ) Notice: Subject to any disclaimer, the term of this patent is extended or adjusted under 35 U.S.C. 154(b) by 289 days.

(21) Appl. No.: 10/566,562

(22) PCT Filed: Jul. 29, 2004

(86) PCT No.: PCT/FR2004/002035

§ 371 (c)(1),
(2), (4) Date: Jan. 31, 2006

(87) PCT Pub. No.: WO2005/012333

PCT Pub. Date: Feb. 10, 2005

(65) Prior Publication Data

US 2006/0183920 A1 Aug. 17, 2006

(30) Foreign Application Priority Data

Jul. 31, 2003 (EP) .................................. 03291931

(51) Int. Cl.
*C07D 209/02* (2006.01)

(52) U.S. Cl. .................................................. 548/452
(58) Field of Classification Search ................. 548/452
See application file for complete search history.

(56) References Cited

U.S. PATENT DOCUMENTS 6,835,843 B2 * 12/2004 Langlois et al. ............ 548/452

FOREIGN PATENT DOCUMENTS

| ES | 8604144 | 6/1986 |
| WO | 0158868 | 8/2001 |
| WO | 03016336 | 2/2003 |

OTHER PUBLICATIONS

International Preliminary Report for PCT/FR2004/002035—Jun. 22, 2006.

* cited by examiner

*Primary Examiner*—Golam M. M. Shameem
(74) *Attorney, Agent, or Firm*—Hueschen and Sage

(57) ABSTRACT

Process for the synthesis of perindopril of formula (I):

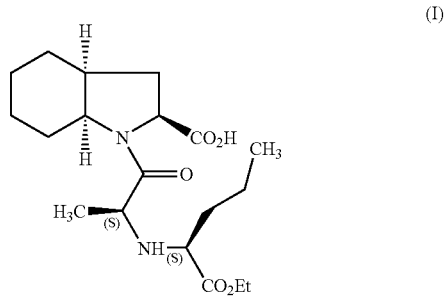

and its pharmaceutically acceptable salts.

6 Claims, No Drawings

METHOD FOR THE SYNTHESIS OF PERINDOPRIL AND THE PHARMACEUTICALLY ACCEPTABLE SALTS THEREOF

The present invention relates to a process for the synthesis of perindopril of formula (I):

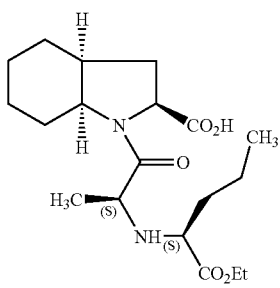

(I)

and its pharmaceutically acceptable salts.

Perindopril and its pharmaceutically acceptable salts, and more especially its tert-butylamine salt, have valuable pharmacological properties.

Their principal property is that of inhibiting angiotensin I converting enzyme (or kininase II), which allows, on the one hand, prevention of the conversion of the decapeptide angiotensin I to the octapeptide angiotensin II (a vasoconstrictor) and, on the other hand, prevention of the degradation of bradykinin (a vasodilator) to an inactive peptide.

Those two actions contribute to the beneficial effects of perindopril in cardiovascular diseases, more especially in arterial hypertension and heart failure.

Perindopril, its preparation and its use in therapeutics have been described in European patent specification EP 0 049 658.

In view of the pharmaceutical value of this compound, it has been important to be able to obtain it by an effective synthesis process, readily transposable to an industrial scale, that leads to perindopril in a good yield and with excellent purity starting from reasonably priced starting materials.

Patent specification EP 0 308 341 describes the synthesis of perindopril by the coupling of (2S,3aS,7aS)-octahydroindole-2-carboxylic acid benzyl ester with N-[(S)-1-carboxybutyl]-(S)-alanine ethyl ester, followed by deprotection of the carboxylic group of the heterocycle by catalytic hydrogenation.

The (2S,3aS,7aS)-octahydroindole-2-carboxylic acid ester is not a commercial product, and its preparation requires several synthesis steps (including a resolution step) starting from indole-2-carboxylic acid.

The Applicant has now developed a new process for the synthesis of perindopril that uses readily obtainable starting materials.

More specifically, the present invention relates to a process for the synthesis of perindopril and its pharmaceutically acceptable salts which is characterised in that a compound of formula (II):

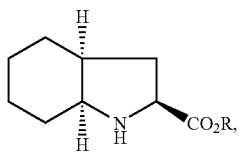

(II)

wherein R represents a hydrogen atom or a benzyl or linear or branched ($C_1$-$C_6$)alkyl group, is reacted with a compound of formula (III) having the (R) configuration:

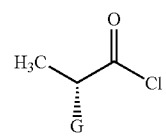

(III)

wherein G represents a chlorine, bromine or iodine atom or a hydroxy, p-toluene-sulphonyloxy, methanesulphonyloxy or trifluoromethanesulphonyloxy group, in the presence of a base, to yield a compound of formula (IV):

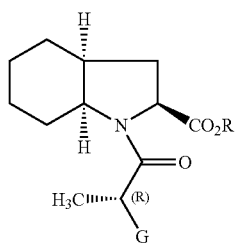

(IV)

wherein R and G are as defined hereinbefore, which is reacted with the compound of formula (V) having the (S) configuration:

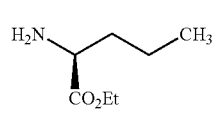

(V)

to yield, after deprotection where necessary, the compound of formula (I).

Among the bases that can be used for the reaction between the compounds of formula (II) and (III) there may be mentioned, without implying any limitation, organic amines, such as triethylamine, pyridine and diisopropylethylamine, and mineral bases, such as NaOH, KOH, $Na_2CO_3$, $K_2CO_3$, $NaHCO_3$ and $KHCO_3$.

When G represents a chlorine, bromine or iodine atom, or a p-toluenesulphonyloxy, methanesulphonyloxy or trifluoromethanesulphonyloxy group, the reaction between the compounds of formulae (IV) and (V) is preferably carried out in the presence of a base, preferably an organic amine, such as triethylamine, pyridine or diisopropylethylamine, or a mineral base, such as $Na_2CO_3$, $K_2CO_3$, $NaHCO_3$ or $KHCO_3$.

When G represents a hydroxy group, the reaction between the compounds of formulae (IV) and (V) is preferably carried out in the presence of an activation reagent, such as N-methyl-N-phenyl-aminotriphenylphosphonium iodide, or hexamethylphosphorus triamide together with ammonium perchlorate, or, when R is other than a hydrogen atom, by Mitsunobu reaction.

The compounds of formula (IV) wherein G represents a chlorine atom or a p-toluenesulphonyloxy or methanesulphonyloxy group are new products which are useful as synthesis intermediates in the chemical or pharmaceutical industry, especially in the synthesis of perindopril, and as such form an integral part of the present invention.

EXAMPLE 1

(2S,3aS,7aS)-1-{(2S)-2-[(1S)-1-(Ethoxycarbonyl) butylamino]-propionyl}octahydro-1H-indole-2-carboxylic acid tert-butylamine salt Step A: Benzyl (2S,3aS,7aS)-1-[(2R)-2-bromopropionyl]octahydro-1H-indole-2-carboxylate Introduce 200 g of benzyl (2S,3aS,7aS)-octahydro-1H-indole-2-carboxylate and 1.5 liters of dichloromethane into a reactor, then bring the temperature of the reaction mixture to 0° C. and add 201 ml of diisopropylethylamine followed by 132 g of (2R)-2-bromo-propionyl chloride. Subsequently, bring the mixture to ambient temperature. After stirring for 1 hour at that temperature, wash the mixture with water and then with a dilute acetic acid solution. The benzyl (2S,3aS,7aS)-1-[(2R)-2-bromopropionyl]octahydro-1H-indole-2-carboxylate solution so obtained is used as it is in the following Step.

Step B: Benzyl (2S,3aS,7aS)-1-((2S)-2-[(1S)-1-(ethoxycarbonyl)butylamino]-propionyl}octahydro-1H-indole-2-carboxylate Introduce 123 g of ethyl (2S)-2-aminopentanoate, 160 ml of triethylamine and 160 ml of acetonitrile into a reactor, and then bring the mixture to 60° C., slowly add the solution obtained in Step A and reflux for 4 hours. After returning to ambient temperature, wash the mixture with water and with a dilute acetic acid solution, and then evaporate off the solvents to yield benzyl (2S,3aS,7aS)-1-{(2S)-2-[(1S)-1-(ethoxycarbonyl)butylamino]-propionyl}octahydro-1H-indole-2-carboxylate.

Step C: (2S,3aS,7aS)-1-{(2S)-2-[(1S)-1-(Ethoxycarbonyl)butylamino]propionyl}-octahydro-1H-indole-2-carboxylic acid Introduce 200 g of the compound obtained in the above Step, in solution in acetic acid, and then 5 g of 10% Pd/C into a hydrogenation vessel. Hydrogenate under a pressure of 0.5 bars at from 15 to 30° C. until the theoretical amount of hydrogen has been absorbed. Remove the catalyst by filtration, and then cool to from 0 to 5° C. and recover by filtration the solid obtained. Wash the cake and dry it to constant weight.

(2S,3aS,7aS)-1-{(2S)-2-[(1S)-1-(ethoxycarbonyl)butylamino]propionyl}-octahydro-1H-indole-2-carboxylic acid is thereby obtained in a yield of 85% and with an enantiomeric purity of 99%.

Step D: (2S,3aS,7aS)-1-{(2S)-2-[(1S)-1-(Ethoxycarbonyl)butylamino]propionyl}-octahydro-1H-indole-2-carboxylic acid tert-butylamine salt The precipitate obtained in the above Step (200 g) is dissolved in 2.8 liters of ethyl acetate, and then 40 g of tert-butylamine and 0.4 liters of ethyl acetate are added.

The suspension obtained is subsequently refluxed until complete dissolution occurs, and the solution obtained is then filtered in the heated state and cooled, with stirring, to a temperature of from 15 to 20° C.

The precipitate obtained is then filtered off, made into a paste again with ethyl acetate, dried and then crushed to yield the expected product in a yield of 95%.

EXAMPLE 2

(2S,3aS,7aS)-1-{(2S)-2-[(1S)-1-(Ethoxycarbonyl) butylamino]-propionyl}octahydro-1H-indole-2-carboxylic acid tert-butylamine salt Step A: (2S,3aS,7aS)-1-[(2R)-2-Bromopropionyl] octahydro-1H-indole-2-carboxylic acid Introduce into a reactor 200 g of (2S,3aS,7aS)-octahydro-1H-indole-2-carboxylic acid, 75 ml of water and 150 ml of toluene, and then bring the mixture to from 0 to 5° C. and add 250 ml of 5M sodium hydroxide solution, followed by a solution of 202 g of (2R)-2-bromopropionyl chloride in toluene, while maintaining the temperature below 10° C. and maintaining the pH of the mixture at 10 by adding 5M sodium hydroxide solution. After stirring for a further 1 hour at 10° C., add concentrated hydrochloric acid to adjust the pH of the mixture to 6.

Separate off the toluene phase, and then add concentrated hydrochloric acid to the aqueous phase to adjust the pH to 2.

The precipitate formed is then filtered off and dried to yield (2S,3aS,7aS)-1-[(2R)-2-bromopropionyl]octahydro-1H-indole-2-carboxylic acid.

Step B: (2S,3aS,7aS)-1-{(2S)-2-[(1S)-1-(Ethoxycarbonyl)butylamino]-propionyl}octahydro-1H-indole-2-carboxylic acid Introduce into a reactor 105 g of ethyl (2S)-2-aminopentanoate, 135 ml of triethylamine and 135 ml of acetonitrile, and then bring the mixture to 60° C. and slowly add a solution of 200 g of the compound obtained in Step A in 1.3 liters of dichloromethane, and subsequently reflux for 4 hours. After returning to ambient temperature, wash the mixture with water and with a dilute acetic acid solution, and then evaporate off the solvents to yield (2S,3aS,7aS)-1-{(2S)-2-[(1S)-1-(ethoxycarbonyl)butylamino] propionyl}octahydro-1H-indole-2-carboxylic acid.

Step C: Identical to Step D of Example 1

EXAMPLE 3

(2S,3aS,7aS)-1-{(2S)-2-[(1S)-1-(Ethoxycarbonyl)butylamino]-propionyl}octahydro-1H-indole-2-carboxylic acid tert-butylamine salt

Step A: Benzyl (2S,3aS,7aS)-1-[(2R)-2-{p-toluenesulphonyloxy}propionyl]-octahydro-1H-indole-2-carboxylate Introduce into a reactor 200 g of benzyl (2S,3aS,7aS)-octahydro-1H-indole-2-carboxylate and 1.5 liters of dichloromethane, and then bring the temperature of the reaction mixture to 0° C. and add 201 ml of diisopropylethylamine, followed by 202 g of (1R)-2-chloro-1-methyl-2-oxoethyl p-toluenesulphonate. Subsequently, bring the mixture to ambient temperature. After stirring for 1 hour at that temperature, wash the mixture with water. The solution of benzyl (2S,3aS,7aS)-1-[(2R)-2-{p-toluenesulphonyloxy}propionyl]octahydro-1H-indole-2-carboxylate so obtained is used as it is in the following Step.

Steps B to D: Identical to Steps B to D of Example 1.

The invention claimed is:

1. A process for the synthesis of a compound of formula (I):

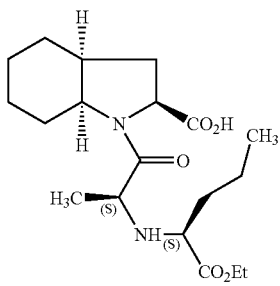

and its pharmaceutically acceptable salts, wherein a compound of formula (II):

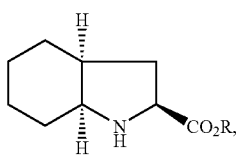

wherein R represents hydrogen, benzyl or linear or branched ($C_1$-$C_6$)alkyl, is reacted with a compound of formula (III) having the (R) configuration:

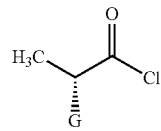

wherein G represents chlorine, bromine, iodine, hydroxy, p-toluenesulphonyloxy, methanesulphonyloxy or trifluoromethanesulphonyloxy, in the presence of a base, to yield a compound of formula (IV):

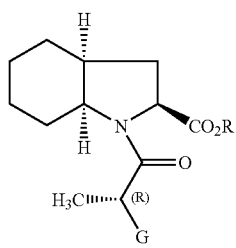

which is reacted with the compound of formula (V) having the (S) configuration:

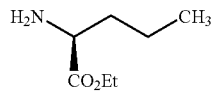

to yield, after deprotection where necessary, the compound of formula (I).

2. A process according to claim 1, wherein the base used for the reaction between the compounds of formulae (II) and (III) is an organic amine selected from triethylamine, pyridine and diisopropylethylamine, or a mineral base selected from NaOH, KOH, $Na_2CO_3$, $K_2CO_3$, $NaHCO_3$ and $KHCO_3$.

3. A process according to claim 1, wherein G represents chlorine, bromine, p-toluenesulphonyloxy, methanesulphonyloxy or trifluoromethanesulphonyloxy.

4. A process according to claim 3, wherein the reaction between the compounds of formulae (IV) and (V) is carried out in the presence of an organic amine selected from triethylamine, pyridine and diisopropylethylamine, or of a mineral base selected from $Na_2CO_3$, $K_2CO_3$, $NaHCO_3$ and $KHCO_3$.

5. A process according to claim 1, wherein G represents hydroxy.

6. A process according to claim 5, wherein the reaction between the compounds of formulae (IV) and (V) is carried out in the presence of an activation reagent selected from N-methyl-N-phenyl-aminotriphenylphosphonium iodide and hexamethylphosphorus triamide together with ammonium perchlorate, or, when R is other than hydrogen, by Mitsunobu reaction.

* * * * *

UNITED STATES PATENT AND TRADEMARK OFFICE
CERTIFICATE OF CORRECTION

PATENT NO.        : 7,358,372 B2                                    Page 1 of 1
APPLICATION NO.   : 10/566562
DATED             : April 15, 2008
INVENTOR(S)       : Claude Fugier et al.

It is certified that error appears in the above-identified patent and that said Letters Patent is hereby corrected as shown below:

On the Title Page, Item (73)
Assignee: "Les Laboratories Servier" should be --Les Laboratoires Servier--.

Signed and Sealed this

Thirty-first Day of March, 2009

JOHN DOLL
*Acting Director of the United States Patent and Trademark Office*